United States Patent
Nicol et al.

(12) 
(10) Patent No.: US 7,097,663 B1
(45) Date of Patent: Aug. 29, 2006

(54) MODULAR PROSTHESIS SYSTEM WITH NOVEL LOCKING MECHANISM

(75) Inventors: Alexander C. Nicol, Glascow (GB); Nicola K. Fowler, Aberfoyle (GB); Donald Christopher Marsden, Cononley (GB)

(73) Assignee: Smith & Nephew, Inc., Memphis, TN (US)

( * ) Notice: Subject to any disclaimer, the term of this patent is extended or adjusted under 35 U.S.C. 154(b) by 232 days.

(21) Appl. No.: 10/022,663

(22) Filed: Dec. 17, 2001

(51) Int. Cl.
*A61F 2/40* (2006.01)

(52) U.S. Cl. .................................. 623/19.13; 623/19.12
(58) Field of Classification Search .............. 623/19.11, 623/19.12, 19.13, 19.14, 19.15, 22.12, 22.42, 623/22.16, 22.4, 22.45; 606/89, 91, 86, 99, 606/102
See application file for complete search history.

(56) References Cited

U.S. PATENT DOCUMENTS

| | | |
|---|---|---|
| 3,694,820 A | 10/1972 | Scales |
| 3,803,641 A | 4/1974 | Golyakhovsky et al. |
| 3,916,451 A | 11/1975 | Buechel et al. |
| 3,978,528 A | 9/1976 | Crep |
| 4,003,095 A | 1/1977 | Gristina |
| 4,040,131 A | 8/1977 | Gristina |
| 4,045,825 A | 9/1977 | Stroot |
| 4,106,130 A | 8/1978 | Scales |
| 4,135,517 A | 1/1979 | Reale |
| 4,179,758 A | 12/1979 | Gristina |
| 4,206,517 A | 6/1980 | Pappas et al. |
| 4,219,893 A | 9/1980 | Noiles |
| 4,279,041 A | 7/1981 | Buchholz |
| 4,301,553 A | 11/1981 | Noiles |

(Continued)

FOREIGN PATENT DOCUMENTS

| | | |
|---|---|---|
| DE | 29 32 744 | 8/1978 |
| DE | 44 01 952 C1 | 1/1994 |
| DE | 4320086 | 12/1994 |
| DE | 195 09 037 | 3/1995 |
| EP | 0 041 591 A1 | 5/1980 |
| EP | 0099167 | 1/1984 |
| EP | 0 127 503 A1 | 12/1984 |
| EP | 0 201 407 A1 | 11/1986 |

(Continued)

OTHER PUBLICATIONS

"Glenohumeral Arthorplasty" p. 148–150.
"Surgical Protocol Modular Shoulder" brochure, 3M Health Care Ltd. 1994.
"Product Speciifcation" brochure, 3M Health Care Ltd. 1994.
"3M Modular Shoulder Ideas in Motion" brochure, 3M Health Care Ltd. 1994.
"Neer II Total Shoulder System" brochure, 3M Health Care Ltd. 1989.
Biomet, Inc.—Shoulder Systems, http://www.biomet/com/products/shoulder.html (© 1997).

(Continued)

*Primary Examiner*—Pedro Philogene
(74) *Attorney, Agent, or Firm*—Kilpatrick Stockton LLP

(57) ABSTRACT

A modular prosthesis for replacement of a joint articulating surface of a bone, where the modular prosthesis generally comprises a head with a recessed socket, an elongate stem, and a connecting member including a patrix member having a generally spherical surface and adapted to be attached to an end of the stem and to be received in the head, and a locking member adapted to lock the head to the stem in a desired orientation; a system for use in surgical repair of a joint including a selection of components for assembling the modular implant prosthesis, a selection of components for assembling a trial prosthesis, and a transfer device for arranging the components of the implant prosthesis in the same orientation as the components of the trial prosthesis; and methods of using the modular prosthesis and system of the invention.

33 Claims, 8 Drawing Sheets

U.S. PATENT DOCUMENTS

| | | | |
|---|---|---|---|
| 4,352,212 A | | 10/1982 | Green et al. |
| 4,524,467 A | * | 6/1985 | DeCarlo, Jr. ............. 623/19.12 |
| 4,538,305 A | | 9/1985 | Engelbrecht et al. |
| 4,549,319 A | | 10/1985 | Meyer |
| 4,608,053 A | | 8/1986 | Keller |
| 4,634,444 A | | 1/1987 | Noiles |
| 4,650,489 A | | 3/1987 | Thompson |
| 4,676,797 A | | 6/1987 | Anaploitis et al. |
| 4,693,723 A | | 9/1987 | Gabard |
| 4,822,370 A | | 4/1989 | Schelhas |
| 4,865,605 A | | 9/1989 | Dines et al. |
| 4,892,546 A | | 1/1990 | Kotz et al. |
| 4,908,032 A | | 3/1990 | Keller |
| 4,911,719 A | | 3/1990 | Merle |
| 4,919,669 A | | 4/1990 | Lannelongue |
| 4,919,670 A | | 4/1990 | Dale et al. |
| 4,921,500 A | | 5/1990 | Averill et al. |
| 4,938,773 A | | 7/1990 | Strand |
| 4,957,510 A | | 9/1990 | Cremascoli |
| 4,963,155 A | | 10/1990 | Lazzeri et al. |
| 4,986,833 A | | 1/1991 | Worland |
| 5,002,578 A | | 3/1991 | Luman |
| 5,002,581 A | | 3/1991 | Paxson et al. |
| 5,015,257 A | | 5/1991 | Crowninshield et al. |
| 5,201,882 A | | 4/1993 | Paxson |
| 5,282,865 A | | 2/1994 | Dong |
| 5,314,479 A | | 5/1994 | Rockwoos, Jr. et al. |
| 5,358,526 A | | 10/1994 | Tornier |
| 5,462,563 A | | 10/1995 | Shearer et al. |
| 5,489,309 A | | 2/1996 | Lackey et al. |
| 5,507,814 A | | 4/1996 | Gilbert et al. |
| 5,507,817 A | | 4/1996 | Craig et al. |
| 5,507,818 A | | 4/1996 | McLaughlin |
| 5,549,682 A | | 8/1996 | Roy |
| 5,549,703 A | | 8/1996 | Daigle et al. |
| 5,580,352 A | | 12/1996 | Sekel |
| 5,658,340 A | | 8/1997 | Muller et al. |
| 5,702,457 A | * | 12/1997 | Walch et al. ............. 623/19.13 |
| 5,702,486 A | | 12/1997 | Craig et al. |
| 5,728,161 A | | 3/1998 | Camino et al. |
| 5,741,335 A | | 4/1998 | Gerber et al. |
| 5,902,340 A | | 5/1999 | White et al. |
| 5,906,644 A | | 5/1999 | Powell |
| 5,910,171 A | | 6/1999 | Kummer et al. |
| 5,944,758 A | | 8/1999 | Mansat et al. |
| 5,989,294 A | * | 11/1999 | Marlow .................. 623/22.16 |
| 6,033,439 A | | 3/2000 | Camino et al. |
| 6,045,582 A | | 4/2000 | Prybyla |
| 6,102,953 A | | 8/2000 | Huebner |
| 6,120,542 A | | 9/2000 | Camino et al. |
| 6,129,764 A | | 10/2000 | Servidio |
| 6,168,627 B1 | | 1/2001 | Huebner |
| 6,171,341 B1 | | 1/2001 | Boileau et al. |
| 6,197,062 B1 | | 3/2001 | Fenlin |
| 6,197,063 B1 | | 3/2001 | Dews |
| 6,203,575 B1 | * | 3/2001 | Farey ..................... 623/18.11 |
| 6,206,925 B1 | | 3/2001 | Tornier |
| 6,228,120 B1 | | 5/2001 | Leonard et al. |
| 6,749,637 B1 | * | 6/2004 | Bahler ..................... 623/19.14 |

FOREIGN PATENT DOCUMENTS

| | | |
|---|---|---|
| EP | 0 201 407 B1 | 11/1986 |
| EP | 0 216 489 A1 | 4/1987 |
| EP | 0 278 807 A3 | 8/1988 |
| EP | 0 299 889 B1 | 1/1989 |
| EP | 0 299 889 A3 | 1/1989 |
| EP | 0 485 311 A1 | 5/1992 |
| EP | 0 639 359 A1 | 8/1993 |
| EP | 0 599 429 A2 | 6/1994 |
| EP | 0 664 108 A2 | 7/1995 |
| EP | 0 679 375 A1 | 11/1995 |
| EP | 0712 617 A1 | 5/1996 |
| EP | 0 850 609 A1 | 7/1998 |
| EP | 0 953 321 A12 | 11/1999 |
| EP | 1 043 001 A2 | 10/2000 |
| EP | 1 048 274 A2 | 11/2000 |
| EP | 1 059 071 A1 | 12/2000 |
| EP | 1 093 777 A2 | 4/2001 |
| FR | 2 617 706 | 1/1989 |
| FR | 2647670 | 12/1990 |
| FR | 2 652 498 | 4/1991 |
| FR | 2 664 809 | 1/1992 |
| FR | 2 685 633 | 7/1993 |
| FR | 2 697 996 | 5/1994 |
| FR | 2 721 200 | 12/1995 |
| FR | 2 727 002 | 5/1996 |
| FR | 2 727 857 | 6/1996 |
| FR | 2 731 612 | 9/1996 |
| GB | 1 292 561 | 10/1972 |
| GB | 1 438 950 | 6/1976 |
| GB | 1 548 750 | 7/1979 |
| GB | 2 223 172 | 4/1990 |
| WO | WO 94/15551 | 7/1994 |
| WO | WO 95/22302 | 5/1995 |
| WO | WO 96/17553 | 6/1996 |
| WO | WO 96/38104 | 12/1996 |
| WO | WO 96/41597 | 12/1996 |
| WO | WO 01/15154 | 3/2000 |
| WO | WO 01/22905 A1 | 5/2001 |

OTHER PUBLICATIONS

DePuy, Product Information: Global™ Total Shoulder System, http://www.depuy.com/product/global.htm (last updated Mar. 13, 1998).

Homedica: MRS, http://www.howmedica.com/mrs/shoulder.htm.

Williamson, Daniel E., Design Consideration in Total Shoulder Arthroplasty Relating to Long–Term Glenohumeral Stability © 1994 Biomet, Inc.).

Fowler, et al., "The development of a modular humeral prosthesis locking mechanism," *Proc. Instn. Mech. Engrs.*, 215(H):229–236 (2001).

Nicol and Fowler, Millennium Shoulder Project, Final Report, Apr. 3, 1998, The University of Strathclyde, Glasgow.

Badet et al., "Arthography and computed arthrotomography study of seventy patients with primary glenohumeral osteoarthritis," *Rev. Rheum. Engl. ed,.* 62(9):55–562 (1995).

Blevins et al, "Dissociation of modular shoulder arthroplasty components," 40th Annual Meeting, Orthopaedic Research Society, New Orleans, p. 827 (1994).

Boileau, et al., "In vitro study of humeral retrotorsion," *J. Shoulder & Elbow Surgery*, 2:512 (1993).

Boileau, "The three–dimensional geometry of the proximal humerus," *JBJS*, 70B:857–865 (1997).

Bonnel, Referenced in "Survey of surgeons to establish details of functional requirements for a new MSS." 3M document (1997).

Buechel et al., "Floating Socket total shoulder replacement: anatomical, biomechanical and surgical rationale," *J of Biomedical Materials Research* 12:89–114 (1978).

Cyprian et al., "Humeral retrotorsion and the glenohumeral relationship in the normal shoulder and in recurrent anterior dislocation (scapulometry)," *Clin. Orthop Rel Res.*, No. 175, 8–17 (1983).

Dahnert et al., "CT measurement of humeral retrotorsion," *Zeitschrift fur Orthopadie und Ihre Granzgebiete*, vol. 124, 46–49 (1986).

Gristina et al., "Monspherical total shoulder replacement," *Iminerva Orthopedica e traumatologica*, vol. 41, Suppl. al N 11, 33–37 (1990).

Harland et al., "Determination of the humeral retrosioun angle," *Zeitschrift fur Orthopadie und Ihre Grenzgebiete*, vol. 129, 36–41 (1991).

Iannotti et al., "Te normal glenohumeral relationships. An anatomical study of 140 shoulders," *JBJS*, vol. 74A, No. 4, 491–500 (1992).

Inman et al., "Observations on the function of the shoulder joint," *JBJS*, vol. 26, 1–30 (1944).

INSERM, Referenced in 'Survey of surgeons to establish details of functional requirements for a new MSS'. 3M document (1997).

Juvinall et al., *Fundamentals of machine component design*, $2^{nd}$ edition, John Wiley & Sons (1991).

Karlsson, "Force distributions in the human shoulder," PhD thesis, Chalmers University of Technology, Gotborg, Sweden (1992).

Kronberg et al., "Retroversion of the humeral head in the normal shoulder and its relationship to the normal range of motion," *Cli. Orthop. Rel Res.*, No. 253, 113–117 (1990).

Kronberg et al., "Stability in relation to humerl head retroversion after surgical treatment of recurrent anterior shoulder dislocations," *Orthopedics*, vol. 16, 281–285 1993).

Maki, "Anthropometric study of the glenhumeral joint," *Trans. Orthop. Res. Soc.* vol. 1, 173 (1976).

McPherson et al, "Anthropometric study of normal glenohumeral relationships," *J. Shoulder & Elbow Surgery*, vol. 6, No. 2, 105–112 (1997).

Morrey et al., Biomechanics of the shoulder, *The Shoulder*, vol. 1, Ed. Rockward CA & Matsen IIFA, WB Saunder Co. (1990).

Neer, *Shoulder Reconstructionl*, Saunders, Philadelphia (1990).

O'Biren et al., "Developmental anatomy of the shoulder and anatomy of the glenohumeral joint," *The Shoulder Ed*, Rockward CA & Matsen III FA, WB Saunders Co. 1–33 (1990).

Pearl et al., "Retroversion of the proximal humerus in relationship to prosthetic replacement arthroplasty," *J. Shoulder & Elbow Surgery*, vol. 7, 286–289 (1995).

Pearl et al., "Coronal plane geometry of the proximal humerus relevant to prosthetic arthroplasy," *J. Shoulder & Elbow Surgery*, vol. 5, No. 4, 320–326 (1996).

Piepper, "Shoulder dislocation in skiing: choice of surgical method depending on the degree of humeral retrotorsion," *Int. J. Sports Med.*, vol. 6, 155–160 (1985).

Poppen et al., "Forces at the glenohumeral joint in abduction," *Clin. Orhtop. Rel Res.*, No. 135, 165–170 (1978).

Randelli et al., "Glenohumeral osteometry by computed tomography in normal and unstable shoulders," *Clin. Orthop. Rel Res.*, No. 208, 151–156 (1986).

Rietveld et al., "The lever arm in glenohumeral abduction after hemiarthroplasty," *JBJS*, 70B, No. 4, 561–565 (1988).

Roberts et al., "The geometry of the humeral head and the design of prosthesis," *JBJS*, 73B, No. 4, 6470650 (1991).

Runciman, *Biomechanical Model of the Shoulder Joint*, PhD. Thesis, Univerisy of Strathclyde (1993).

Saha, "Dynamic stability of the Glenohumeral joint," *Acta. Orthop. Scandinav.*, vol. 42, 491–505 (1971).

Sarrafian, Gross and functional anatomyof the shoulder, *Clin. Orthop. Rel Res.*, No. 173, 11–19 1983).

Soderlund et al, Radiologic assessment of humeral head retroversion, *Acta Radiological*, vol. 30, 501–505 (1989).

Symeonides et al., "Humeral head torsion in recurrent anterior dislocation of the shoulder," *JBJS*, 77B, No. 5, 687–690 (1995).

Testut, *Traite' d'Anatomie Humaine*, $7^{th}$ edition, vol. 1: Osteologie, arthologie, Myologie, Paris (1921).

Randelli et al, "Glenohumeral osteometry by computed tomography in normal and unstable shoulders," *Clin. Orthop. Rel Res.*, No. 208, 151–156 (1986).

Fowler, et al., "The development of a modular humeral prosthesis locking mechanism," *Proc. Instn. Mech. Engrs.*, 215(H):229–236 (2001).

Nicol and Fowler, Millennium Shoulder Project, Final Report, Apr. 3, 1998, The University of Strathclyde, Glasgow.

Badet et al., "Arthography and computed arthrotomography study of seventy patients with primary glenohumeral osteoarthritis," *Rev. Rheum. Engl. ed.*, 62(9):55–562 (1995).

Blevins et al, "Dissociation of modular shoulder arthroplasty components,"$40^{th}$ Annual Meeting, Orthopaedic Research Society, New Orleans, p. 827 (1994).

Bolleau, et al., "In Vitro study of humeral retrotorsion," J. Shoudler & Elbow Surgery, S12 (Jan./Feb. 1993) (Abstract).

Boileau, "The three–dimensional geometry of the proximal humerus,"*JBJS*, 70B:857–865 (1997).

Buechel et al., "Floating Socket' total shoulder replacement: anatomical biomechanical and surgical rationale," *J of Biomedical Materials Research* 12:89–114 (1978).

Cyprian et al., "Humeral retrotorsion and the glenohumeral relationship in the normal shoulder and in recurrent anterior dislocation (scapulometry)," *Clin. Orthop Rel Res.*, No. 175, 8–17 (1983).

Dahnert et al., "CT measurement of humeral retrotorsion," *Zeitschrift fur Orthopedie und Ihre Granzgebiete*, vol. 124, 46–49 (1986).

Gristina et al., "Monspherical total shoulder replacement," *Iminerva orthopedica e traumatologica*, vol. 41, Suppl. al N 11, 33–37 (1990).

Harland et al., "Determination of the humeral retrosioun angle," *Zeitschrift fur orthopadie und Ihre Granzgebiete*, vol. 129, 36–41 (1991).

Iannotti et al., "Te normal glenohumeral relationships. An anatomical study of 140 shoulders," *JBJS*, vol. 74A, No. 4, 491–500 (1992).

Inman et al., "Observation on the function of the shoulder joint," *JBJS*, vol. 26, 1–30 (1944).

Juvinall et al., *Fundamentals of machine component design*, $2^{nd}$ edition, John Wiley & Sons (1991).

Kronberg et al., "Retrovision of the humeral head in the normal shoulder and its relationship to the normal range of motion," *Cli. Orthrop. Rel Res.*, No. 253, 113–117 (1990).

Kronberg et al., "Stability in relation to humerl head retroversion after surgical treatment of recurrent anterior shoulder dislocations," *Orthopedics*, vol. 16, 281–285.

Maki, "Anthropometric study of the gleno humeral joint, "$22^{nd}$ Annual ORS, Braniff Place Hotel, New Orleans, Louisana p. 173 (Jan. 28–30, 1976) (Abstract).

McPherson et al, "Anthropometric study of normal glenohumeral relationships,"*J. Shoulder & Elbow Surgery*, vol. 6, No. 2, 105–112 (1997).

Morrey et al., "Biomechanics of the shoudler," Chapter 6, pp. 208–245 The Shoulder, Ed. Rockward CA & Matsen III FA, WB Saunders Co. (1990).

Neer, "Glenohumeral Arthoplasty," Shoulder Reconstruction,Chapter 3, pp. 143, 148, 149, 150, Ed. W.B. Saunders Company (1990).

O'Brien et al., "Development anatomy of the shoulder and anatomy of the glenohumeral joint," Chapter 1, *The Shoulder*, Ed. Rockward CA & Masten III FA, WB Saunders Co. 1–33 (1990).

Pearl et al., "Retroversion of the proximal humerus in relationship to prosthetic replacement arthoplasty," *J. Shoulder & Elbow Surgery*, vol. 7, 286–289 (1995).

Pearl et al., "Coronal plane geometry of the proximal humerus relevant to prosthetic arthroplasty," *J. Shoulder & Elbow Surgery*, vol. 5, No. 4, 320–326 (1996).

Piepper, "Shoulder dislocation in skiing: choice of surgical method depending on the degree of humeral retrotorsion," *Int. J. Sports Med.*, vol. 6, 155–160 (1985).

Poppen et al., "Forces at the glenohumeral joint in abduction," *Clin. Orthop. Rel Res.*, No. 135, 165–170 (1978).

Randelli et al, "Glenohumeral osteometry by computed tomography in normal and unstable shoulders," *Clin. Orthop. Rel Res.*, No. 208, 151–156 (1986).

Rietveld et al., "The lever arm in glenohumeral abduction after hemiarthroplasty," *JBJS*, 70B, No. 4, 561–565 (1988).

Roberts et al., "The geometry of the humeral head and the design of prothesis," *JBJS*, 73B, No. 4, 6470650 (1991).

Saha, "Dynamic stability of the Glenohumeral joint," Acta. Orthrop. Scandinav., vol. 42, 491–505 (1971).

Sarraflan, "Gross and functional anatomy of the shoulder," *Clin. Orthop. Rel Res.*, No. 173, 11–19 1983) .

Soderlund et al, "Radiologic assessment of humeral head retroversion," *Acta Radiologica*, vol. 30, 501–505 (1989).

Symeonides et al., "Humeral head torsion in recurrent anterior dislocation of the shoulder,"JBJS, 77B, No. 5, 687–690 (1995).

Randelli et al., "Glenohumeral osteometry by computed tomography in normal and unstable shoulders," *Clin. Orthop. Rel Res.*, No. 208, 151–156 (1986).

Thesis by Karisson, Dan, Force Distributions in the Human Shoulder, Chalmers University of Technology, Division of Mechanics (1992).

3M Health Care Product Specification brochure, 3M Health Care Limited, LowtonWay, Hellaby Industrial Estate, Rotherham S66 8RY, DBGE147AA, 5 pp. (1994).

3M Modular Shoulder Ideas in Motion brochure, 3M Orthopaedic Products 3M Health Care Limited, 3M House, Morley Street, Loughborough, Leicestershire Le11 1EP, 2 pages (1994).

Biomet Bio–Modular Total Shoulder. . . Developed in conjunction with Russell R. Warre, M.D. and David M. Dines, M.D., 8 pages (1992).

Depuy Global Total Shoulder Arthoplasty System. . . Experience A New Dimension In Design. . . Design Rationale and Surgical Technique, pp. 2–27.

* cited by examiner

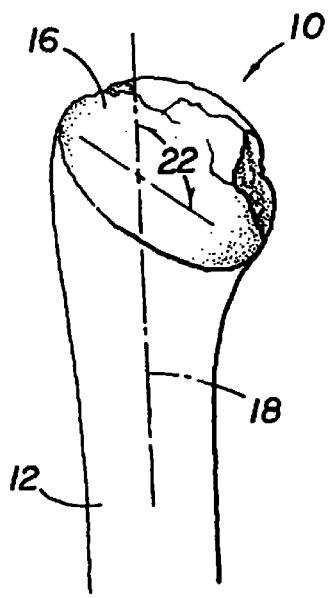
FIG 1
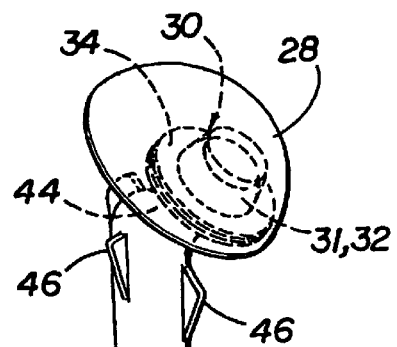
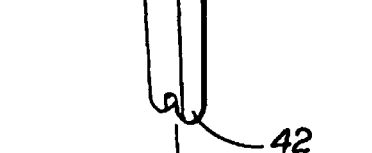
FIG 2
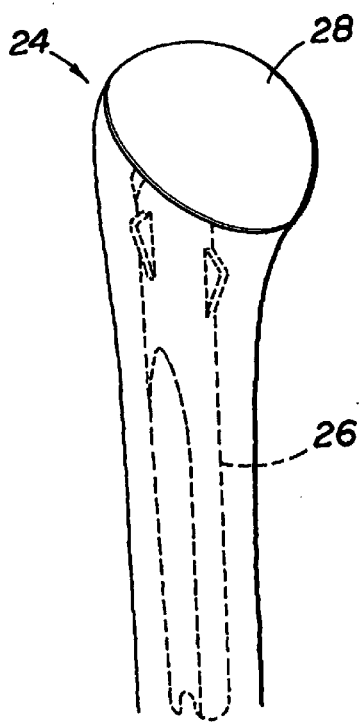
FIG 3

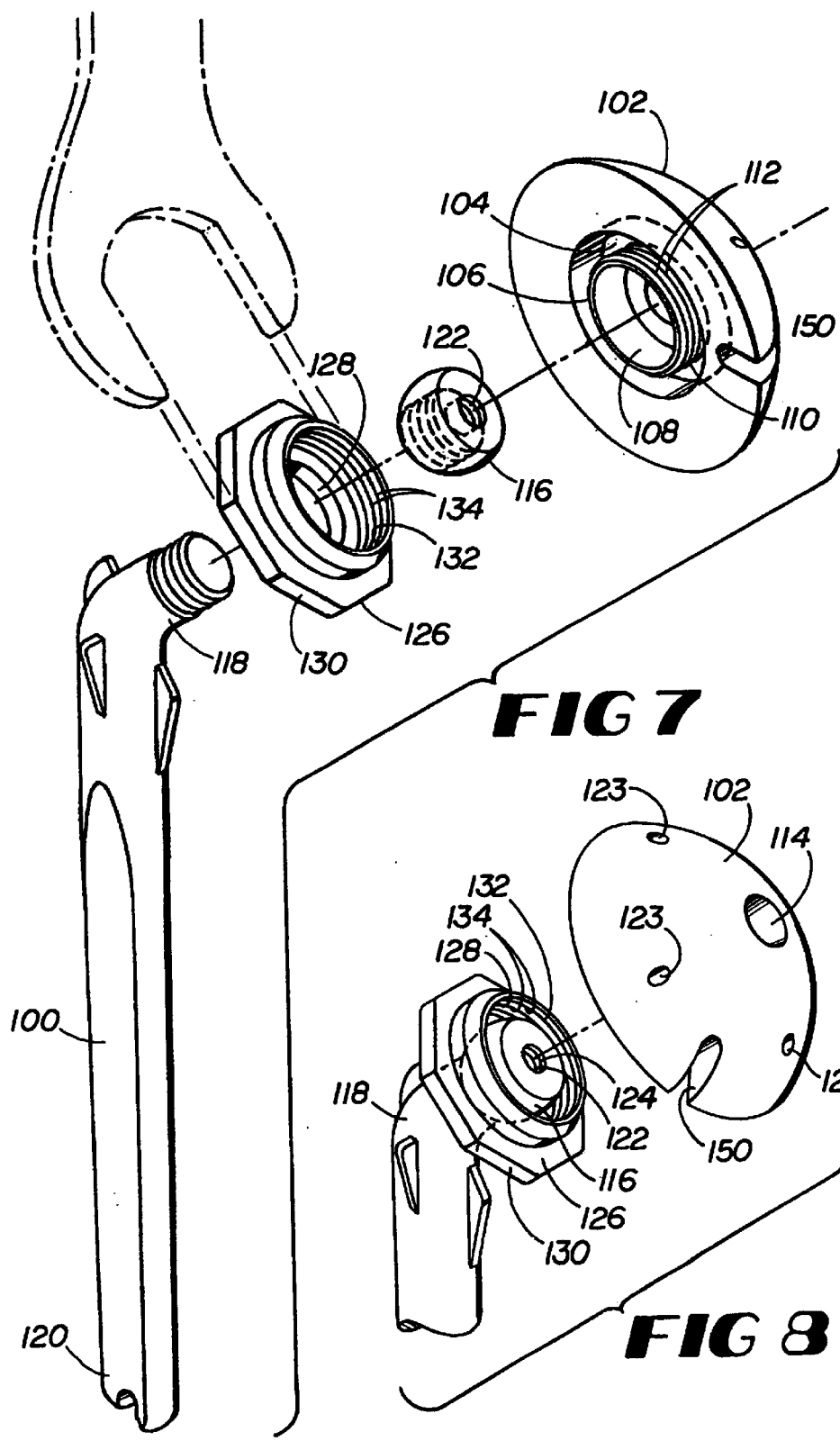

MODULAR PROSTHESIS SYSTEM WITH NOVEL LOCKING MECHANISM

FIELD OF THE INVENTION

The present invention relates to an improved modular prosthesis for use in complete or partial joint replacement and repair where various component parts of the prosthetic implant are independently selected to allow the surgeon to custom fit the implant to a patient's anatomy without requiring a large inventory of components of various sizes and shapes, where the components are connected by a connecting member that allows continuous, multi-dimensional variation of the component parts to achieve a desired orientation, and where, once positioned, the parts are securely locked in place with a novel locking mechanism for securely locking the components in the desired orientation. The present invention further relates to methods of using the modular prosthesis and locking mechanism to repair or replace all or a portion of a damaged joint.

BACKGROUND OF THE INVENTION

Patients suffering from trauma or disorders causing severe joint pain often require surgical treatment involving complete or partial replacement of the affected joint. For instance, disorders of the gleno-humeral or shoulder joint may require the surgeon to replace the components of the patient's joint with prosthetic parts. During a shoulder replacement operation, at least a portion of the proximal section of the humeral shaft is replaced by a metal prosthesis. This prosthesis generally consists of two parts: a stem that is mounted into the medullary canal of the humerus, and a head retaining component connected in some manner to the stem. The head retaining component replaces the bearing surface of the humerus and articulates within the glenoid cavity of the scapula to allow movement of the shoulder.

In such operations, surgeons increasingly want to be able to custom fit prostheses to patients without having to choose a properly sized prosthesis from a large group of preformed one-piece, or "monobloc," implants. Use of monobloc implants requires the surgeon to maintain a large inventory of such implants and allows the surgeon to custom fit the implant only within pre-set parameters.

Modular prostheses are known where the stem and head retaining component may be supplied in "modular" form, that is, as separate connectable components. Different stem sizes and head sizes in modular implant design provide the surgeon with some degree of inter-operative flexibility. A range of stem and head sizes allows the surgeon to choose a particular combination to suit the anatomy of each individual patient without having to maintain a large inventory of integral or "monobloc" prostheses. However, while these prior modular prostheses accommodate variations in patients' bone structure that arise due to differences in bone size and shape, they do not address variations in the angles and orientation of the skeletal system among individual patients. For example, in the case of the proximal humerus, individual patients require differing resection angles, i.e., angles of inclination of the humeral head relative to the stem, differing angles of retroversion or anteversion of the head, and differing degrees of lateral and/or posterior offsets between the axis of the head and the axis of the stem.

Other modular humeral prostheses have accommodated such variability between patients by a variety of adjustable connectors for linking the head to the stem or by surgical kits containing a wide range of connectors from which to select that fix the appropriate offset, resection angle, and angle of anteversion/retroversion. However, these solutions have drawbacks in that either they require a large number of connectors for mixing and matching with the various sized stems and heads, or the adjustable connectors are limited to adjustment in specific increments or enable adjustment of only a single variable or along only one or two rotational axes.

Prior humeral prosthetic implants have used ball joints in place of the traditional taper lock, or "Morse taper," design for connecting the humeral stem and humeral head to provide a continuous range of possible arrangements of the head with respect to the stem. This type of joint makes it possible to define the most favorable resection angle, angle of anteversion and lateral offset of the humeral head. However, prior prostheses with ball joints secure the ball with various means requiring the use of small screws.

One prior art ball joint uses a set screw to engage a recess on the surface of the ball to hold the ball in place within a spherical cavity. This method of securing the ball is counterproductive because although the ball contains multiple recesses for engaging the screw, this arrangement limits the possible orientations of the ball in relation to the head and stem, thereby undermining the primary advantage of the ball joint—the capacity for continuous adjustment between the stem and head of the prosthesis.

Another example employs a slotted spherical ball and a screw plus a conical push rod designed to expand the ball to lock it within a spherical cavity in either the stem or the head. Such locking mechanisms have disadvantages in that the small blind hole required for the screws used in such mechanisms can collect debris which can fester and cause infection. Additionally, the small screws are difficult to handle during surgery and create a risk of becoming lost in the soft tissue of the patient. Furthermore, set screws concentrate the locking force on a small surface area rather than distributing it uniformly over a greater area. This concentrated stress can create more debris, thereby increasing the risk of infection.

Many prior prostheses incorporating a spherical ball joint have other drawbacks as well, such as difficulty creating a secure lock to prevent the components from slipping under pressure from high loads. This is most likely because prior ball joints house the ball in a generally spherical socket on either the humeral stem or humeral head. Such spherical sockets are designed to contour the geometry of the ball. This type of design has not demonstrated optimal torque to slip rates in laboratory studies designed to simulate the maximum expected torque loads on the joint during strenuous activities.

Thus, there is a need for a modular prostheses that allows continuous, three-dimensional variation of the orientation of the component parts, that reduces the number of standard component parts required to achieve optimal fixation, and that can be securely locked in a desired position without the use of small screws and with the ability to resist maximum expected loads without slippage. It would also be advantageous to have a basic prosthesis design that may be modified by using basic component parts that may be mixed and matched and then further adjusted relative to each other to allow reconstruction of the original anatomy of the patient. It would also be advantageous to provide a humeral prosthesis design made of modular parts which that may be independently selected to approximate the natural anatomy of the patient's proximal humerus for a shoulder replacement.

SUMMARY OF THE INVENTION

Methods, devices and instrumentation of this invention seek to provide a modular prosthesis for use in complete or partial joint replacement and repair that allows continuous variation of the orientation of the component parts to replicate the natural anatomy of the patient's joint and that includes a novel locking mechanism for securely locking the components in place in the desired orientation. With the modular prosthesis of the invention, a continuous range of possible arrangements and orientations of the component parts is possible without requiring a multitude of various components, and a secure lock between components is achieved without the use of small screws which may become lost or cause infection.

Methods, devices and instrumentation according to this invention more particularly provide a modular prosthesis designed to replace the joint articulating surface of a bone, i.e. the portion of a bone which forms the bearing surface of the joint requiring replacement or repair; a modular prosthesis kit for replacement and repair of all or a portion of the damaged joint; and methods for using the modular prosthesis of the invention to replace or repair the damaged joint. In one embodiment, the primary components of the modular prosthesis include a stem, a head, a connecting member for positioning and attaching the stem and the head in a desired orientation, and a locking member for securely locking the components together.

A modular prosthesis according to the present invention includes a prosthetic head chosen to suit a patient's joint articulating surface and the surface of the resected bone and is attached to a stem chosen to suit the medullary canal of the resected bone by a connecting member including a patrix member having a generally spherical surface and a locking member. In one embodiment, the patrix member is attached to the proximal end of the stem, and the prosthesis head includes a socket recessed into the underside of the head for housing the patrix member. As used herein, "patrix member" refers to a projection, or male member, which is adapted for attachment to the stem and to be received in the recessed socket of the head. The generally spherical surface of the patrix member provides the connecting surface between the head and the stem and allows the head to be rotated with respect to the stem about multiple axes, thus providing a virtually unlimited range of possible orientations of the stem and head and the ability to custom fit the prosthesis to the anatomy of the patient. In one embodiment of the invention the patrix member is a generally spherical ball attached to the end of the stem.

The novel locking member is designed to retain the patrix member within the head socket, once the components have been positioned as desired, by holding the patrix member between the locking member and the head socket with a force sufficient to lock the patrix member securely and rigidly in place relative to the stem and the head. This force is distributed substantially uniformly on at least one ring of contact between the patrix member and the locking member and at least one ring of contact between the patrix member and the head socket to form a secure lock between the head, patrix member and stem.

In one embodiment, the locking member is a locking ring that fits around the proximal end of the stem and is adapted to be received within a cylindrical cavity in the undersurface of the prosthetic head. This cylindrical cavity is concentric to the head socket that receives the patrix member. When the patrix member is placed in the head socket and positioned as desired, the locking ring is then moved into the cylindrical cavity of the head and thus engages the head and a portion of the patrix member, such that when engaged, the combination of the force of the locking ring against the patrix member, on at least one ring of contact between the patrix member and the locking ring, and the corresponding force of the head against the patrix member, on at least one ring of contact between the patrix member and the head socket, stabilizes the head and subsequently locks the stem and head combination together. The locking ring and the head thus contact the patrix member on at least two rings, distributing the stress of the locking force substantially uniformly around those rings, which reduces the risk of infection from debris created by concentrated point contact as with prior art locking devices such as set screws.

In one embodiment, the patrix member is welded to the proximal end of the stem, and the locking ring is positioned on the neck of the stem just below the patrix member. Additionally, the locking ring is placed on the stem prior to welding the patrix member to the stem. This arrangement and the ease of manipulating the ring into position prevents the possibility of losing the locking ring during the surgical procedure prior to locking the humeral head and stem in the desired arrangement, as is possible with the use of small, loose screws. The locking ring also eliminates the need for small holes in the prosthesis that allow accumulation of debris, which can then fester and cause infection. Furthermore, the locking ring allows greater surface area of contact between the ring, patrix member, and head, which minimizes debris caused by concentrated point contact and consequently reduces the risk of infection caused by such debris. Additionally, optimization of the surface finish on the surface area of contact between the components allows for greater friction between the contacting surface and thus more securely immobilizes the stem and head in the desired angular position.

In one embodiment of the invention, the head socket, which houses the patrix member, has a frusto-conical, i.e. tapered, shape to allow for greater control over the angle of contact between the patrix member and the head. Preferably, the interior geometry of the locking ring, which fits up against the patrix member when the locking ring is engaged, is also frusto-conical. The dual cone shape, or dual taper, of the head socket and the ring of this embodiment provide control over the contact position of the patrix member, allow more room for the head socket within the head, and allow for a larger patrix member to be used. In this embodiment, the dual cones are designed so that the angle of contact between the head and the patrix member is less than the angle of contact between the ring and the patrix member, which increases the locking ability of the device. The optimization of the contact angles provides improved torque to slip ratios, thus providing a prosthesis which will withstand maximum anticipated loads without slipping.

The locking potential between the components of a modular prosthesis according to the invention may be further enhanced by employing different surface finishes on the contact areas of the components. In one embodiment of the invention, the patrix member is divided into two areas of different surface finish. The surface area of the patrix member that contacts the interior of the head socket has a rough finish, and the surface of the head socket has a corresponding rough finish. The surface area of the patrix member that contacts the interior wall of the locking ring has a smooth finish, and the surface of the interior wall of the locking ring has a corresponding smooth surface. The relative coefficient of friction values play an important role in the locking function; thus, optimization of the interplay between the surface finishes provides for increased friction locking between the components which enhances the overall locking strength of the device.

Methods, devices and instrumentation according to this invention even more particularly provide a modular humeral prosthesis for replacing the proximal portion of the humerus in which an elongate stem is adapted to be received in the medullary canal of a resected humerus. The head of the humeral prosthesis has a generally hemispherical shaped outer surface that corresponds to the glenoid cavity of a human scapula. The connecting member includes a patrix member having generally spherical surface at the proximal end of the stem designed to correspond to a socket on the underside of the humeral head retaining component. The patrix member is preferably welded to the proximal end of the stem. The stem/patrix member/head assembly is then secured in a desired orientation by a locking member. The locking member may be any mechanism that retains the patrix member within the head socket, between the locking member and the head socket, with a force sufficient to lock the patrix member securely and rigidly in place relative to the stem and head, where the force is distributed around at least one ring of contact between the patrix member and the locking member and at least one ring of contact between the patrix member and the head socket, thereby creating a secure lock between the patrix member and the head and the patrix member and the locking member. In one embodiment the patrix member is a generally spherical ball and the locking member is a locking ring that is fitted around the neck of the shaft just distal to the ball and is preferably placed on the stem prior to attaching the ball to the stem.

An additional aspect of this invention is a surgical kit that includes a selection of components of various sizes and shapes for assembling the permanent, or implant, prosthesis, a corresponding selection of trial components for assembling and testing a trial prosthesis, and a transfer jig for assembling the components of the implant prosthesis to match the arrangement and orientation of the trial prosthesis.

Another aspect of this invention seeks to provide a method of using the modular prosthesis for replacing or repairing all or a portion of a damaged joint and orienting the components of the prosthesis to compliment the patient's natural anatomy. More particularly, this invention provides a method for replacing or repairing the proximal humerus and humeral head with the modular prosthesis of the invention.

These and other features of this invention will become apparent after a review of the following detailed description of the disclosed embodiments.

BRIEF DESCRIPTION OF THE DRAWINGS

FIG. 1 is a perspective view of a fractured or diseased humerus.

FIG. 2 is a exploded perspective view of a resected humerus and a modular prosthesis of the invention.

FIG. 3 is a perspective view showing the prosthesis of FIG. 2 implanted in the resected humerus.

FIG. 7 is a fully exploded perspective view of a trial prosthesis of the invention.

FIG. 8 is a perspective view of the trial stem assembly of FIG. 7 with the trial head exploded away.

DETAILED DESCRIPTION OF THE PREFERRED EMBODIMENTS

Figure 4:
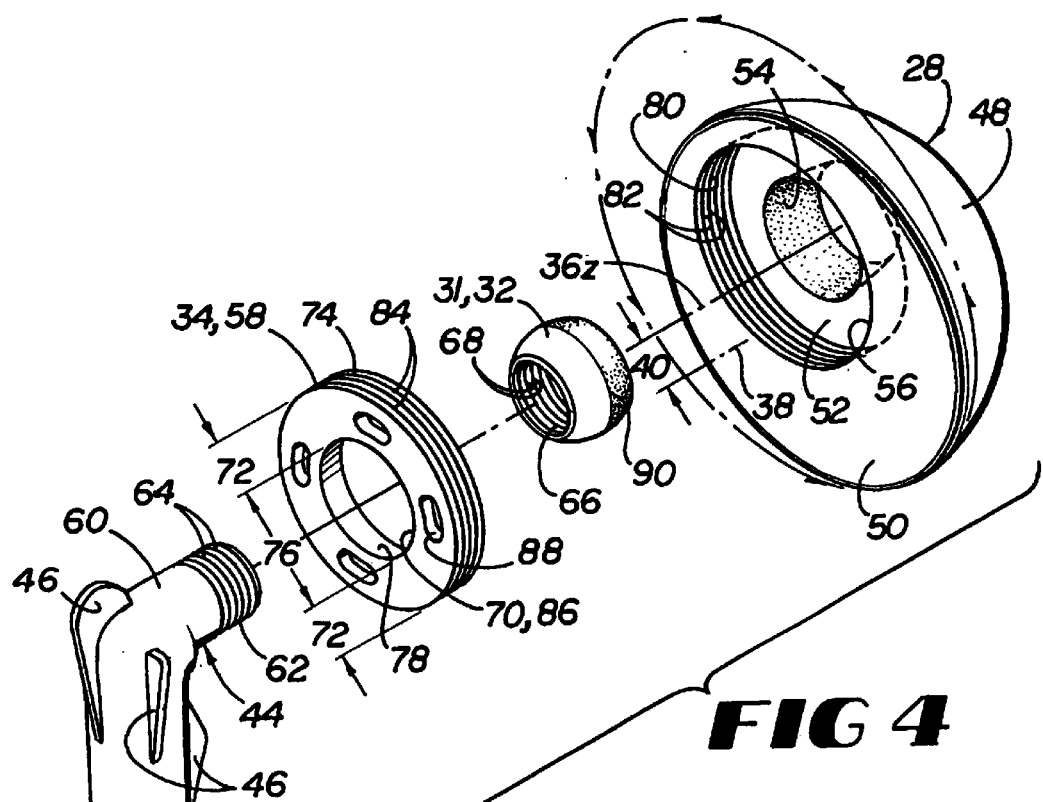
FIG. 4 is a fully exploded view of a modular prosthesis of the invention.

Methods, devices, and instrumentation according to this invention seek to improve orthopedic surgical procedures for joint replacement and repair as well as the performance of orthopedic prostheses used to replace and repair the bones that form the articulating surfaces and components for the joint requiring treatment. Methods, devices, and instrumentation according to this invention provide a modular prosthesis for use in complete or partial joint replacement and repair that allows continuous, multi-dimensional adjustment of the orientation of the prosthesis components, thereby allowing the surgeon to position the components to replicate the natural anatomy of the patient's joint. The modular prosthesis of the invention includes a novel locking mechanism for securely locking the components in place in the desired orientation while distributing the locking force substantially uniformly on the contact surface between the components, providing an improved friction lock between the components and minimizing concentrated point contact, debris and the capacity for infection inherent in the use of small screws.

A modular prosthesis of the invention is designed to replace the proximal end of the bone that forms the bearing surface of the joint requiring replacement or repair. FIG. 1 depicts an intact humerus 10, with a shaft 12, medullary canal 14, and damaged humeral head 16. The shaft axis 18 and the dotted line representing the proposed resection surface 20 define the resection angle 22. The literature offers two methods for defining the resection angle of a humeral neck. FIG. 1 depicts the resection angle as defined by the largest angle between the plane of the resected bone (shown as line 20) and the humeral shaft axis (line 18), as set forth by Ianotti et al. (1992), INSERM (1997) and Pearl & Volk (1996). A modular prosthesis according to one embodiment of this invention is designed to approximate the geometry of the end of a bone which has been resected to accommodate a prosthesis. The primary components of the modular prosthesis of the invention are a stem, a head, and a connecting member for positioning and attaching the stem and the head in a desired orientation and including a locking member for securely locking the components together. The prosthesis of this invention is preferably made of cobalt-chromium alloys or implantable titanium alloys, but may be made of any metals or other materials known to those in the art as suitable for implantation in a patient.

Consider one example of instrumentation and devices according to this invention. FIG. 2 illustrates one embodiment of the modular prosthesis according to this invention disposed above a resected humerus 24, and FIG. 3 depicts the prosthesis of FIG. 2, which has been implanted into a resected humerus 24. Generally, a modular prosthesis of this invention includes an elongate stem 26, a head 28, and a connecting member 30 which includes a patrix member 31, having a generally spherical surface, and a locking member 34.

As used herein, the term "head" means the prosthesis head which is designed to replicate and replace the bearing surface of the bone which articulates in the joint requiring treatment. For instance, in a surgical treatment for repair of the gleno-humeral joint, i.e. the shoulder, the prosthesis head replaces the humeral head of the humerus, which articulates in the glenoid cavity of the scapula. As used herein, the term "patrix member having a generally spherical surface" or "patrix member" means a projection or male member that has a generally spherical surface and that is adapted for attachment to an end of the stem. In the embodiment of the invention shown in the figures, the patrix member 31 is a generally spherical ball. As used herein, the term "generally spherical ball," "spherical ball," or "ball" means a portion of the connecting member that has a substantially spherical shape but which may not be a perfect or complete sphere. For instance, a portion of the sphere may be removed at one end such that the ball has a flat surface, as shown in FIGS. 4 through 9.

The prosthesis of the invention accommodates a wide range of variation, in a relatively inexpensive manner, by providing three dimensional variability by using a connecting member having a generally spherical surface, rather than a plurality of intermediate connecting members. This combination allows the surgeon to optimize the orientation of the head and stem to approximate the anatomical variations of a particular patient. For instance, in reconstructing a shoulder with a prosthesis according to this invention, the ability of the patrix member to allow rotation of the humeral head with respect to the stem along three axes, optionally combined with a small offset of the rotational axis of the humeral head from the center of the patrix member, allows the surgeon to adjust the angle of inclination (or resection angel), angle of anteversion (or retroversion) and the lateral offset of the humeral head required in orienting the stem and head to custom fit the prosthesis to a patient's natural anatomy.

Figure 5:
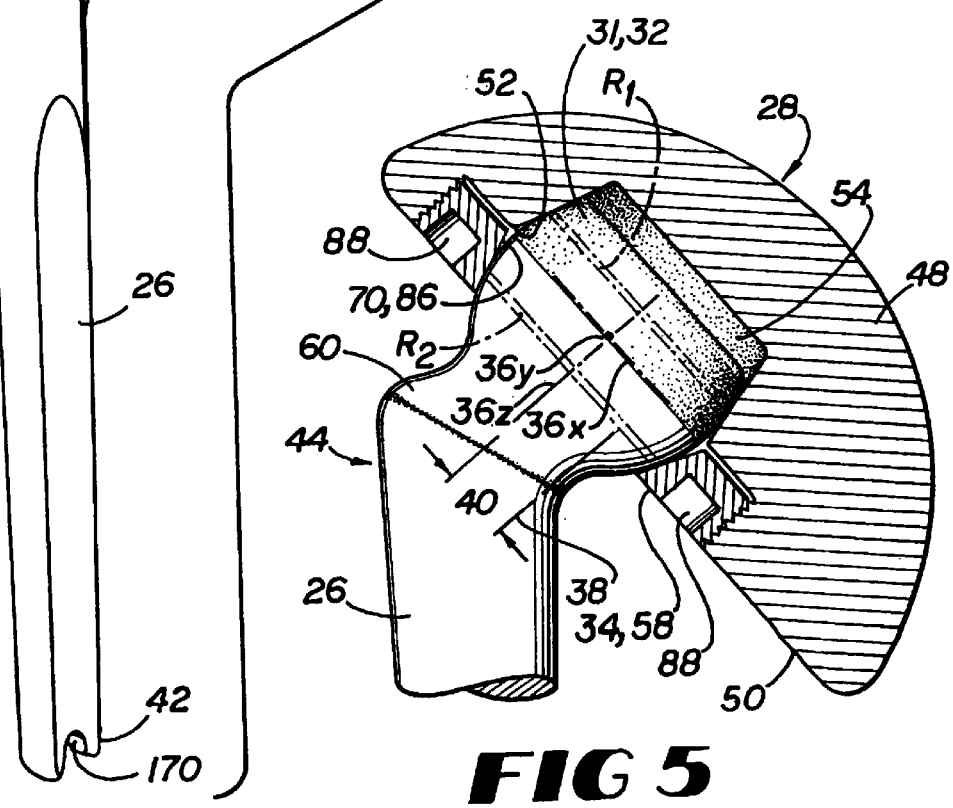
FIG. 5 is a cross sectional view of another embodiment of a modular prosthesis of the invention.

FIG. 5 illustrates the rotational motions of the head 28 by subdividing the motion into three basic rotations about 3 primary axes. In the embodiment shown, the patrix member is a generally spherical ball and the center of rotation 36 of the generally spherical ball 32 is offset from the center of rotation 38 of the head 28, by a distance 40. The offset may be from approximately 2 mm to approximately 12 mm, more preferably from approximately 3 mm to approximately 5 mm. Because of the offset 40, rotation of the head 28 about axis 36z allows adjustment of the lateral offset of the head. This rotation also provides some interdependent adjustment in the posterior direction, allowing for provision of a posterior offset present in some patients. The posterior offset may be from approximately 0 mm to approximately 10 mm, preferably from approximately 0 mm to approximately 5 mm.

Rotation of the head about axis 36y enables tilting of the head 38 which allows adjustment of the resection angle. One embodiment of a prosthesis of the invention allows a range of adjustment of the resection angle from about 130° to about 150°; another embodiment allows a resection angle from about 125° to about 155°; and a third embodiment allows adjustment from about 120° to about 160°. The lateral retroversion of the head may be controlled by rotation of the head about the axis 36x. The possible range of adjustment of the angle of retroversion provided by one embodiment of a prosthesis of the invention is from about 15° to about 40°. Another embodiment of the prosthesis of the invention allows retroversion of the head from about 10° to about 50°.

Figure 6:
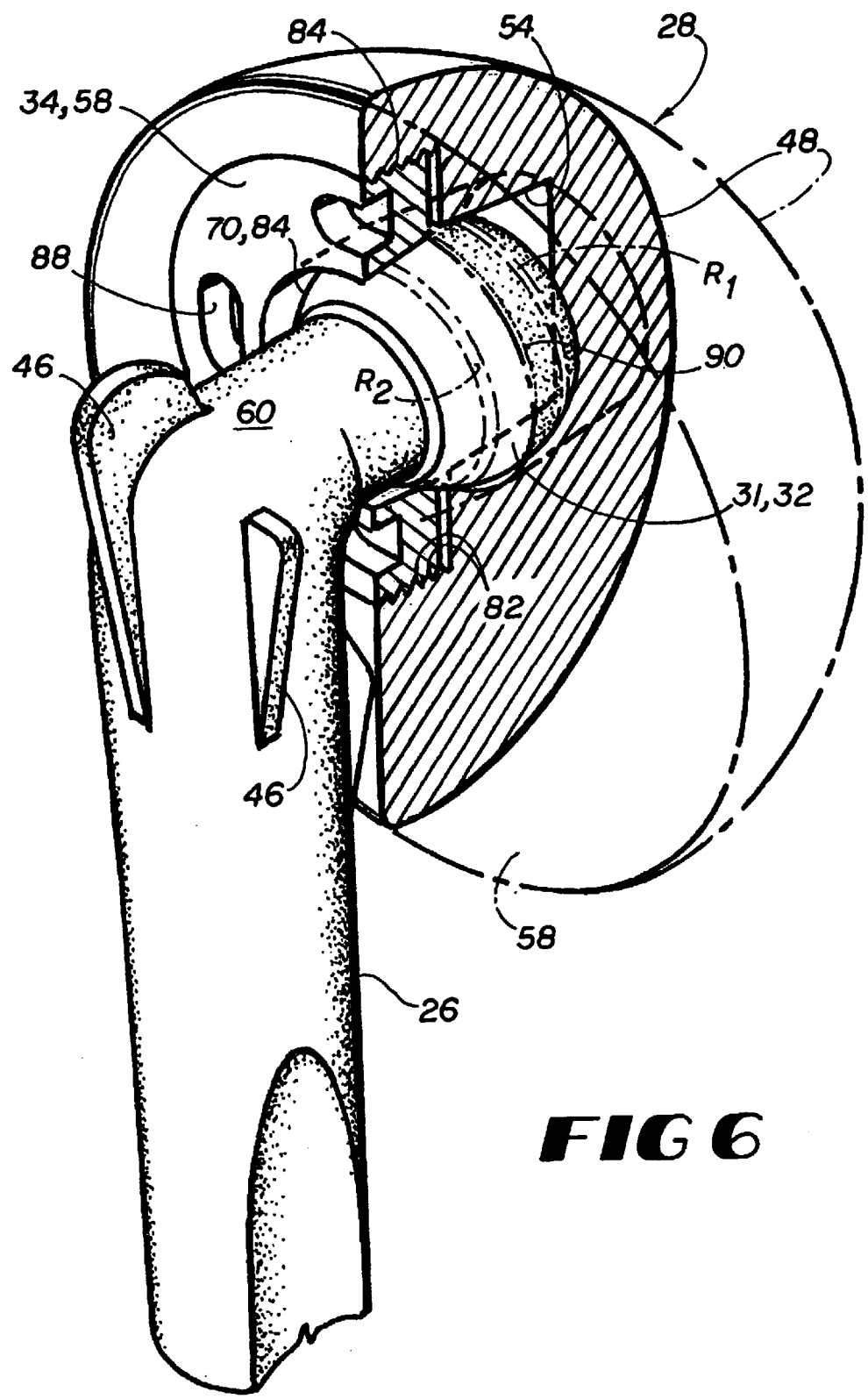
FIG. 6 is a partially cross-sectioned perspective view of the assembled modular prosthesis of FIG. 4 or 5.

FIGS. 4 through 6 depict one embodiment of a modular prosthesis according to the invention. For purposes of illustration, the prosthesis depicted in the figures is a humeral prosthesis; however, it will be recognized by those of skill in the art that the invention is not limited to a humeral prosthesis. As shown in the figures, the prosthesis includes a stem, head and a connecting member, including a patrix member having a generally spherical surface and a locking member. In the figures the patrix member is a generally spherical ball, but the patrix member may be any projection, or male member, that has a generally spherical surface. The locking member shown is a locking ring; however, the locking member may be any mechanism capable of locking the ball securely in place by compressing the ball on two rings, where the locking force is substantially evenly distributed along the rings.

The stem 26 of the modular prosthesis is generally elongate and is adapted to fit within the medullary canal 14 of a resected bone 24, as shown in FIGS. 2 and 3. The stem may be various lengths and thicknesses to accommodate the requirements of the patient's anatomy. The stem is generally from about 115 mm to about 250 mm in length. The diameter of the stem is generally from about 6 mm to about 16 mm. It should be understood by one of skill in the art that these ranges apply generally to the embodiment shown in the figures, adapted for implantation into a human humerus, and will be adjusted for various embodiments of the invention, particularly for prostheses according to the invention adapted to be used in larger bones or non-human patients. The stem has a first end 42 that is received in the medullary canal 14 of a resected bone 24 and a second end 44 adapted to cooperate with a prosthesis head. The diameter of the stem should generally correspond to the diameter of the medullary canal of the resected bone. The stem may also have fins 46 at the proximal end to prevent the rotation of the stem within the medullary canal once implanted.

In the modular prosthesis according to the present invention, a prosthetic head 28 is selected from a variety of shapes and sizes to approximate the configuration of the head of the patient's bone at the end of the bone that functions as the bearing surface of the bone within the joint to be repaired. For the embodiment shown in the figures, the height of the head may be from approximately 12 mm to approximately 33 mm, preferably from approximately 14 mm to approximately 33 mm. The radius of the head in the embodiment shown generally ranges from approximately 23 mm to approximately 29 mm. The outer surface 48 of the head 28 is shaped to correspond with the surface of the joint with which it articulates. The undersurface 50 of the head is adapted to correspond with the resection surface of the resected bone and to cooperate with the second end of the stem. In one embodiment of the invention, the undersurface of the head comprises a cavity 52 concentric with a socket 54 for receiving the connecting member 30.

In an embodiment of a prosthesis according to the invention, the generally spherical ball 32 is preferably attached to the second end 44 of the elongate stem 26 and adapted to cooperate with the prosthesis head 28. The undersurface of the head has a recessed portion, or cavity, 52 which is optionally offset, or eccentric, to, the rotational axis of the head, as described above. The cavity 52 is adapted to receive the locking member 34 and the generally spherical ball 32. The cavity includes a socket 54 for housing the spherical ball 32. The socket is preferably concentric to the cavity, and the cavity preferably includes a locking surface 56 for engaging a corresponding locking surface on the locking member.

The head socket 54 is designed to house the stem ball 32, such that the head 28 may be placed on the stem ball and then oriented as desired. The locking member 34 is adapted to engage the assembled head and stem, such that when engaged, the stem ball 32 is compressed by the locking member against the inside of the head socket 54, and the combined force of the head and the locking member on the stem ball stabilize the construct and subsequently lock the stem and head combination together in a fixed position. The locking member 34 may be any mechanism that compresses the ball on two rings such that the locking force is substantially evenly distributed around the rings to create a secure lock between the ball and the head and the ball and the locking member.

In one embodiment, as shown in FIG. 5, the locking member 34 is a locking ring 58 positioned around the neck 60 of the stem just distal to the spherical ball 32 and that may be positioned on the stem prior to welding the ball to the stem, as shown in FIG. 5 by weld line 92. In another embodiment, shown in FIG. 4, the second end 44 of the stem 26 is a threaded male end 62, with threads 64, and the spherical ball 32 has an axial bore 66 with threads 68, such that the locking ring 58 may be placed on the stem 26 and the ball 32 may be subsequently screwed on to the threaded male end of the stem 62. This embodiment provides the added advantage of requiring only one ball and locking ring to fit any stem size, as opposed to providing each stem with its own ball and locking ring.

When engaged, the locking ring 58 contacts the head cavity 52 and the undersurface of the spherical ball 32 to create an upward force of the locking ring and a corresponding downward force of the head, which combine to hold the ball 32 securely in a desired position. In other words, the ball is compressed on two rings and the locking force is distributed substantially uniformly around these rings to provide a strong lock between the head and the stem. As depicted in FIGS. 5 and 6, the first ring $R_1$ is formed by the contact of the ball 32 with the head socket 54 and the second ring $R_2$ is formed by the contact of the ball 32 with the inner wall 78 of the locking ring 58. In the embodiments shown in the figures, the rings $R_1$ and $R_2$ are substantially parallel, but alternate embodiments, in which the nature of the locking member, patrix member, and head socket and the angles of contact between these components form rings of contact that are not necessarily parallel to one another, are within the scope of the invention.

As shown in FIG. 4, the locking ring 58 has a generally cylindrical geometry with an axial bore 70 for accommodating the stem neck 60 and the undersurface of the spherical ball 32. The outer diameter 72 of the locking ring defines an outer wall 74, and the inner diameter 76 (the diameter of the axial bore) defines an inner wall 78. The outer wall may have a locking surface for engaging a corresponding locking surface 56 on the inner wall 80 of the cavity 52 located on the undersurface of the prosthesis head. The inner wall 78 of the locking ring is preferably shaped to accommodate a portion of the spherical ball.

In the embodiment of the invention shown in FIGS. 4–6, the geometry of the cavity 52 on the underside of the prosthesis head is generally cylindrical to correspond to the circular shape of the locking ring 58. The inner wall 80 of the cylindrical cavity 52 corresponds to the outer wall 74 of the locking ring 58, and preferably includes a locking surface for engaging a corresponding locking surface on the outer wall of the locking ring. In one embodiment, the locking surface comprises threads 82 circling the inner wall 80 of the cylindrical cavity 52 for engaging corresponding threads 84 on the outer wall 74 of the locking ring 58. The head cavity 52 preferably also has a socket 54, which is preferably concentric to the cylindrical cavity 52 that forms a housing for receiving the spherical ball 32 of the stem.

The head socket 54 may be any shape designed to accommodate and hold the spherical ball of the stem; shapes include, but are not limited to, concave, hemispherical, arched, and conical. The socket of the embodiment shown in FIGS. 4–6 has a frusto-conical, i.e. tapered, geometry for improved locking. The frusto-conical socket allows for greater control over the angle of contact between the ball and the head. The resulting optimization of the contact angle affords improved torque to slip ratios, thus providing a prosthesis that will withstand maximum anticipated loads without slipping.

The axial bore 70 of the locking ring 58 through which the stem passes is designed to correspond to the underside of the spherical ball when the locking ring is engaged. In one embodiment, as best illustrated in FIG. 5, the ring 58 has a tapered bore 86, such that diameter of the bore 86 is smaller at the stem end and larger at the ball end to accommodate the portion of the ball closest to the stem neck. The direction of the taper of tapered bore 86 of locking ring 58 is opposite that of the frusto-conical socket 54 of the humeral head 28, which is widest at the socket opening and decreases towards the head interior. When the ball and head are disposed as desired relative to one another, the locking ring is locked into place by engaging the locking surface on the ring with the locking surface on the recessed portion of the humeral head. The combination of the force of the locking ring against the ball, on at least one ring of contact between the ball and the locking ring, and the corresponding force of the humeral head, on at least one ring of contact between the ball and the socket of the humeral head, effectively locks the ball within the socket of the humeral head.

The locking ring also includes a driving surface on the underside of the locking ring for manipulating the ring to lock it within the head. In one embodiment, the external driving member is an external hex, or other external shape capable of bearing a torque load, adapted to engage a corresponding driver. In another embodiment, as shown in FIGS. 4–6, the external driving surface is one or more external slots 88 adapted to engage a torque wrench.

In one embodiment of the invention, the ball 32 is divided into two areas of different surface finish that correspond to the surface finish of the contact surfaces on the head socket and the locking ring. As shown in FIGS. 4–6, the ball 32 is divided by an equator 90. Above the ball equator 90, the surface finish is substantially rough, as is the corresponding surface of the head socket. The surface finish of the components is described herein in terms of microns (µm) and is the measure of the average distance, or height, of microscopic peaks and valleys on the surfaces of the components. As used herein "rough surface" or "substantially rough," means from approximately 2 µm to approximately 4 µm, more preferably approximately 3.2 µm. The surface of the ball below the line 90, where the ball surface contacts the interior wall of the locking ring, has a smooth finish, and the surface of the interior wall of the locking ring has a corresponding substantially smooth surface. As used herein "smooth surface" or "substantially smooth," means from approximately 0.1 μm to approximately 1 cam, preferably approximately 0.8 μm. The resulting interplay between the surface finishes, and thus the corresponding coefficient of friction values, provides for improved friction locking between the components, which enhances the overall locking strength of the device.

Methods, devices and instrumentation according to this invention further seek to provide a surgical kit for replacement of a damaged joint, including: a selection of prosthesis stems of various lengths and diameters for accommodating the medullary canal of a patient's bone, each having a first end adapted for insertion into the medullary canal of the bone, a second end attached to a patrix member having a generally spherical surface, and a locking ring fitted around the second end of the stem; prosthesis heads of various heights and diameters, each having a recessed socket for housing the patrix member of a selected stem; trial stems of various lengths and diameters corresponding to the prosthesis stems and each having a patrix member and a locking member, such as a locking ring, similar to that of the permanent, or implant, prosthesis, but having an external locking mechanism, such as an external hex to enable easy locking of the components while implanted in a patient's bone; trial heads of various heights and diameters, which are preferably made of plastic and color coded to correspond to the different head sizes; and a transfer jig for assembling the implant prosthesis to match the orientation of the trial prosthesis.

Figure 9:
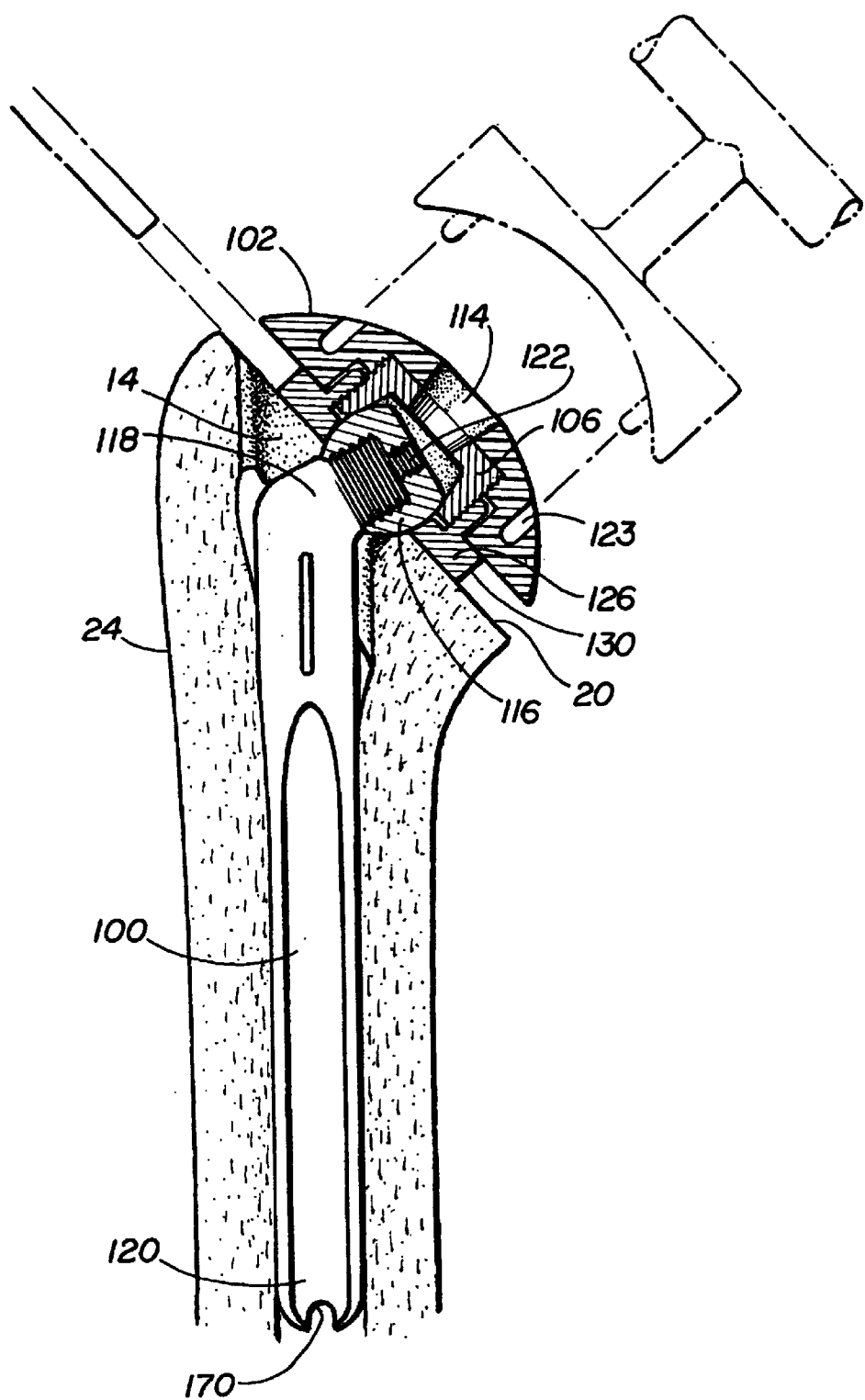
FIG. 9 is a cross-sectional view of the assembled trial implant of FIG. 7 or 8 inserted in a resected humerus.

One embodiment of a trial prosthesis of the present invention is shown in FIGS. 7–9. The trial stem 100 is generally similar to the implant stem and should be provided in the same height and diameter ranges as the implant stems. The trial head 102 should also be provided in the same heights and diameter ranges as the implant heads; however, the trial heads are preferably made of plastic and are preferably color coded according to head size for ease of identification. In the embodiment shown, the patrix member is a generally spherical ball and the locking member is a locking ring.

Like the implant head, the underside of the trial head also includes a cavity 104 for receiving a patrix member and locking ring. The cavity on the trial head has a cylindrical geometry for receiving a metal socket 106. The metal socket 106 is fixed within the cylindrical cavity 104 and has a diameter smaller than the diameter of the cylindrical cavity. In the embodiment shown, the socket is tapered like that of the implant head depicted in FIGS. 4 through 6. The metal socket 106 has and internal surface 108 for receiving the spherical ball of the trial prosthesis, an external surface 110 with threads 112 for engaging the trial locking ring, which fits in the space between the cylindrical cavity 104 and the metal socket 106. The trial head also includes an axial bore 114 that extends through the outer surface of the head, the cylindrical cavity and the metal socket, for accommodating a device for extracting the assembled trial prosthesis.

In the trial prosthesis, one embodiment of which is shown in FIGS. 7 and 8, the patrix member is a generally spherical ball 116 that is attached to the second end 118 of the trial stem 100. In contrast to the implant ball 32, ball 116 includes an axial bore 112 with threads 124 for receiving a device for extracting the assembled trial prosthesis from the patient's bone when the device is inserted through the axial bore in the trial head to engage the threaded axial bore 122 of the ball 116. The trial prosthesis also has a locking ring 126 with an axial bore 128 for accommodating the trial stem 100 and a portion of the trial ball 116. The trial locking ring 126 also has an external hex 130, which allows the surgeon easily to lock the trial components in a desired location while implanted in the patient's bone. In the embodiment shown, the external hex 130 is larger than the diameter of the ring 126 and the diameter of the bore 128 through the hex is smaller than the axial bore of the ring. The ring 126 has an inner wall 132 that corresponds to the external surface 110 of the metal socket 106 of the trial head 102. The trial ring 126 also includes threads 134 on the inner wall 132 for engaging the threads 112 on the external surface 110 of the metal socket 106 of the trial head 102. FIG. 9 depicts the trial prosthesis shown in FIGS. 7 and 8 inserted into a resected humerus. Possible embodiments of devices used to manipulate the trial prosthesis while implanted are shown in phantom lines. The trial prosthesis of the invention may be used in methods according to the invention for surgical replacement of a joint articulating surface.

Methods, devices and instrumentation according to this invention further seek to provide a method for using the modular prosthesis of the invention in a surgical procedure to repair a damaged joint. Even more particularly the invention provides a method for using a modular humeral prosthesis of the invention to repair a shoulder by replacing the proximal humerus with a humeral prosthesis according to the invention. One method of using one embodiment of this invention to replace a joint articulating portion of a bone is as follows. The end of the damaged bone is resected to remove the patient's natural humeral head in order to accommodate the prosthesis. A trial prosthesis according to the invention is selected, which has a stem chosen to correspond to the length and width of the medullary canal of the resected bone. The stem of the trial prosthesis includes a patrix member having a generally spherical surface and a locking ring with an external hex for driving the locking ring, as described above. A trial prosthesis head retaining component is chosen to approximate the size and shape of the patient's natural humeral head. The components are loosely assembled by lightly screwing the locking ring into the trial head.

The first end of the trial prosthesis stem is then inserted into the medullary canal of the patient's bone, and the proximal end of the stem to which the patrix member and locking ring are attached protrudes from the resection surface of the bone, as shown in FIG. 9. The trial head retaining component is then rotated about the patrix member to achieve the desired resection angle, angle of anteversion and medio-lateral and posterior offset. After the surgeon determines the desired orientation of the head, a driver adapted to engage the external hex of the trial prosthesis is used to tighten the locking ring within the cylindrical cavity of the head to lock the components in that position. Once locked, the surgeon may manipulate the patient's bone to simulate movement of the bone within the joint to test the selected components and orientation. The surgeon may also choose to test multiple head sizes and shapes during the trial procedure; thus, the trial head may be removed and replaced easily without removing the trial stem. When a desired head has been selected and the orientation of the components has been determined, the components are locked in place and the trial prosthesis is extracted from the bone.

Figure 10:
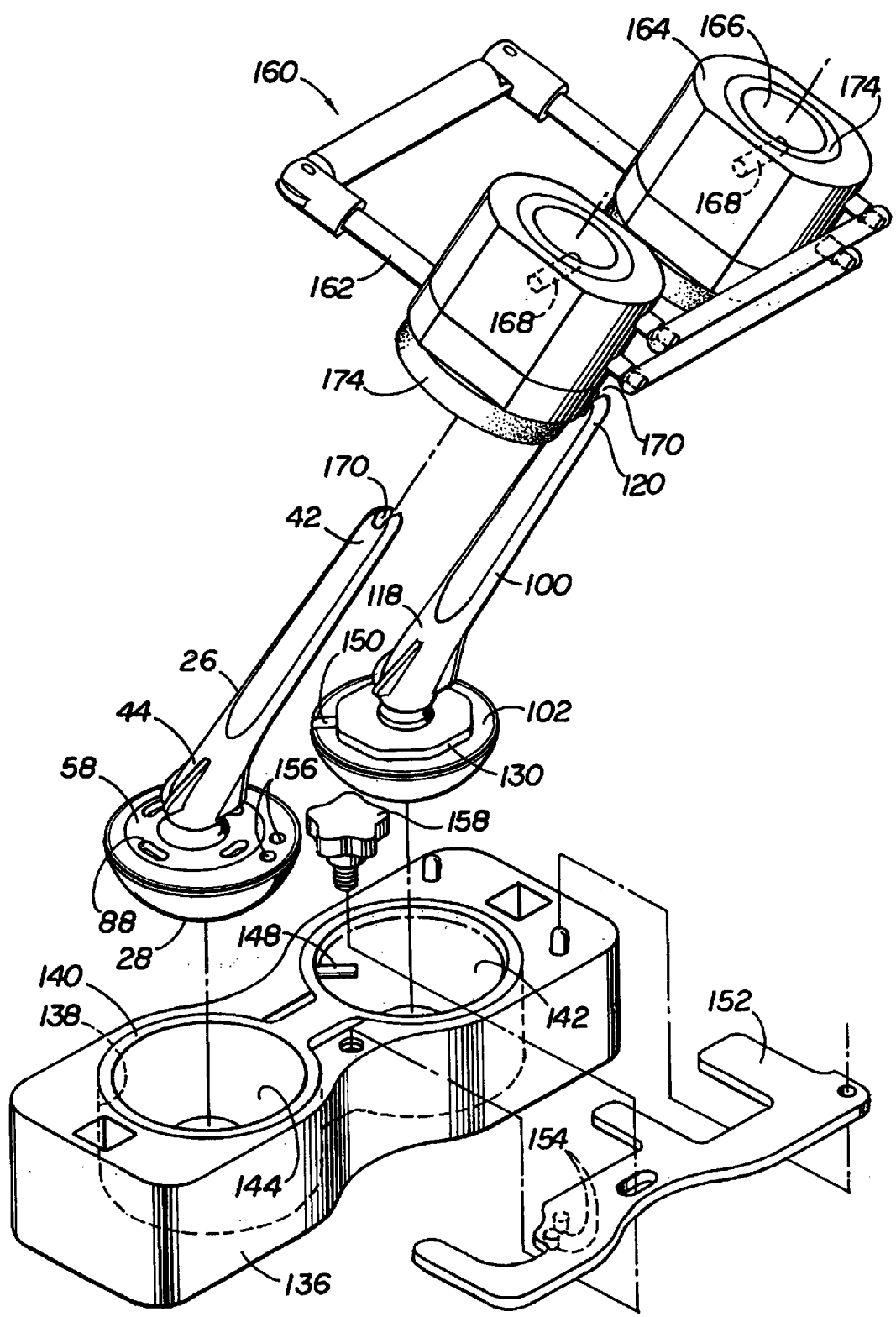
FIG. 10 is an exploded perspective view of a trial prosthesis and implant prosthesis of the invention and a transfer device of the invention.

The extracted trial prosthesis is then mounted in a transfer jig, or transfer device, which allows the surgeon to determine the exact orientation of the components of the trial prosthesis and then to assemble the components of the implant prosthesis to correspond to the orientation of the trial prosthesis. The transfer device depicted in FIGS. 10–13 comprises a base unit 136 with a recession 138 adapted to accommodate a head retaining component 140. The head retaining component comprises two concave surfaces 142 and 144 for receiving the both the trial and implant prosthesis heads, respectively, and is specific to head size. The head retaining component is preferably made of colored plastic and is color coded to correspond to the head size of the trial prosthesis, and hence the implant prosthesis as well. The concave surface 142 that receives the trial head 102 has a bar 148 on one side of the concave surface that engages a slot 150 on the underside of the trial head to orient the trial head in a set position, as shown in FIG. 10. An implant stem and head are chosen to correspond to the size and shape of the trial head and stem and loosely assembled by lightly tightening the locking ring.

Figure 11:
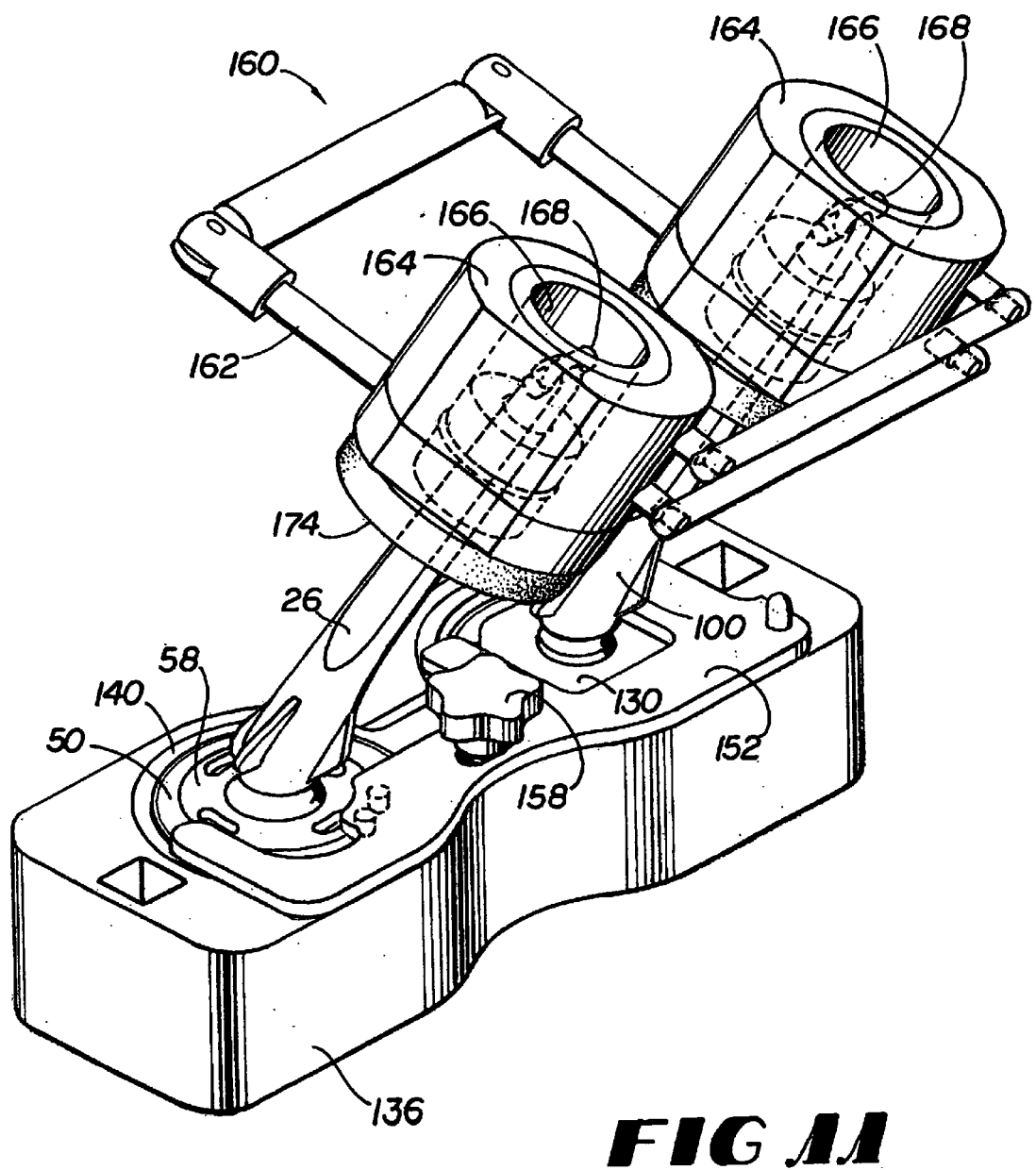
FIG. 11 is a perspective view of the trial and implant prostheses of FIG. 9 mounted in the transfer device of FIG. 10.
Figure 12:
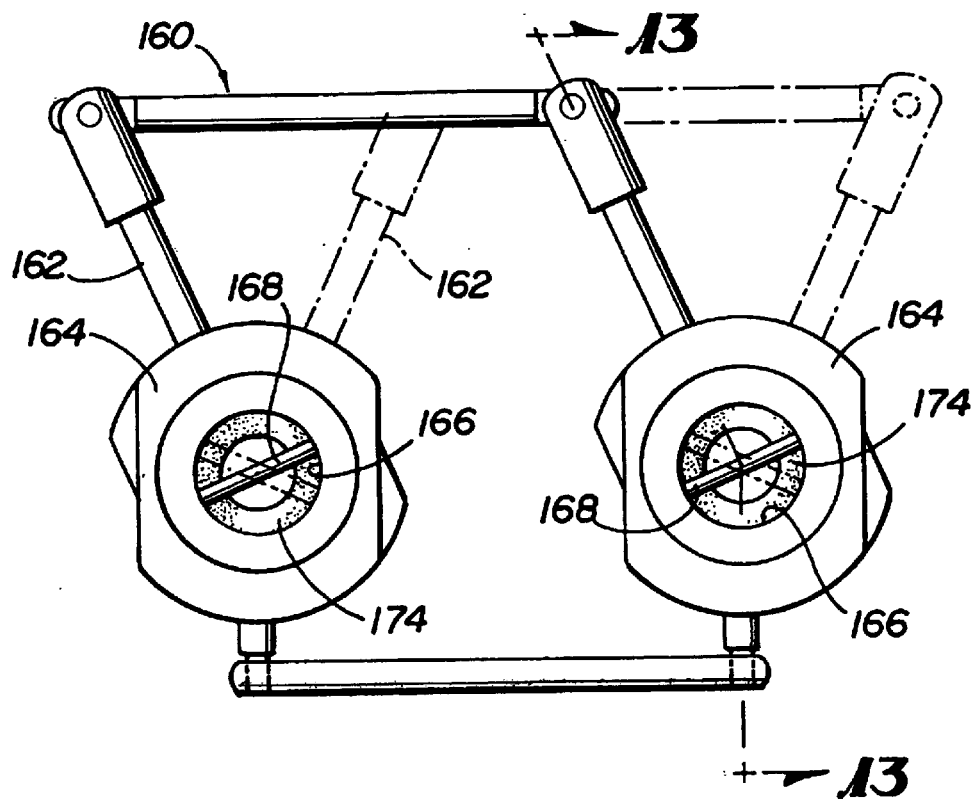
FIG. 12 is a plan view of the stem or component of the transfer device of FIGS. 10 and 11.
Figure 13:
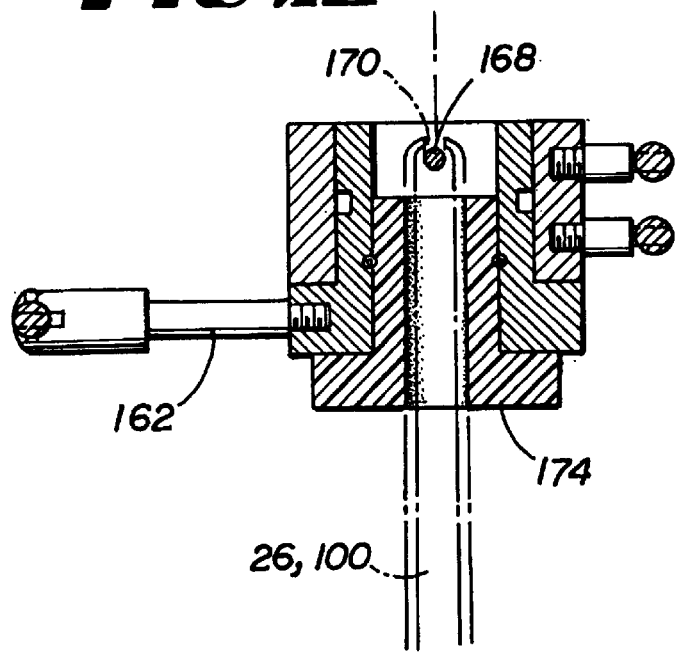
FIG. 13 is a cross-sectional view taken substantially along lines 13—13 in FIG. 12.

The implant prosthesis is then placed, head down, in the second concave surface 144 adjacent to the trial prosthesis. When positioned, the undersurface of the heads should be flush with the top surface of the base unit. A plate 152 is placed over the heads as shown in FIG. 11. The plate comprises two pins 154 for engaging two holes 156 on the undersurface of the implant head for orienting the implant head in a set position that corresponds to the set position of the trial head. A thumb screw 158 allows the plate to be moved toward the base unit to immobilize the heads with in the base unit.

A stem unit 160 is then used to engage the stems of the trial and implant prosthesis and to allow the surgeon to position the stem of the implant prosthesis to match the orientation of the trial stem. The stem unit, depicted in greater detail in FIGS. 12 and 13, includes a four-bar unit 162 connecting two cylinders 164, which are adapted to receive and retain the stems of the prostheses contained in the transfer device. The cylinders 164 are hollow to accommodate cylinder inserts 174 which are selected to accommodate the stem diameters. The cylinder inserts 174 are preferably made of plastic and color coded to correspond to the appropriate stem size. The cylinder inserts 174 each have an axial bore 166 for receiving the two stems. The cylinders 164 each have a bar 168 for engaging a slot 170 in the first end of each stem to retain the stems within the cylinders 164. The surgeon then uses the four-bar linkage 162 to move the cylinders 164 containing the stems in order to engage and orient the implant stem into a position corresponding with the position of the trial stem.

While the implant prosthesis is positioned and held rigidly in place by the plate pins 154, a driver is used to engage external slots 88 on the underside of the locking ring of the implant prosthesis. A sufficient torque is applied to the driver to lock the locking ring into place in the head with a desired locking force. After the components are securely locked in place, the implant prosthesis is removed from the mounting device, the stem of the prosthesis is inserted into the medullary canal of the resected bone and the surgeon reconstructs the soft tissue of the affected joint.

The foregoing description of the preferred embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

What is claimed is:

1. A modular prosthesis for at least partial replacement of a joint articulating surface of a bone, comprising:
    a) a head having a first surface adapted to cooperate with a joint surface and a second surface adapted to cooperate with an elongate stem, the second surface comprising a recessed socket;
    b) an elongate stem adapted to be implanted within the medullary canal of a resected long bone, the stem having a first end that is adapted to be received within the medullary canal of the resected bone and a second end adapted to cooperate with the prosthetic head;
    c) a connecting member for securely connecting the stem and head in a desired orientation, comprising
        a patrix member having a generally spherical surface attached to the second end of the stem and adapted to be received in the head socket, wherein the generally spherical surface of the patrix member allows orientation of the head and stem relative to multiple axes; and
        a locking member adapted to lock the head to the stem in a desired orientation, wherein the locking member retains the patrix member within the socket between the locking member and the head socket with a force sufficient to lock the patrix member securely and rigidly in place relative to the stem and the head, wherein the force is distributed around at least one ring of contact between the patrix member and the locking member and at least one ring of contact between the patrix member and the head socket.

2. The modular prosthesis of claim 1, wherein the head socket is offset from the center of rotation of the head, and the center of rotation of the patrix member is eccentric to the center of rotation of the head.

3. The modular prosthesis of claim 1, wherein the head further comprises a cavity for receiving the locking member.

4. The modular prosthesis of claim 3, wherein the cavity is concentric with the head socket.

5. The modular prosthesis of claim 3, wherein the cavity comprises an inner wall, the inner wall further comprising a locking surface for engaging a corresponding locking surface on the locking member.

6. The modular prosthesis of claim 5, wherein the locking surface comprises threads.

7. The prosthesis of claim 1, wherein the locking member comprises a locking ring having an axial bore for receiving the second end of the elongate stem and a portion of the patrix member.

8. The prosthesis of claim 7, wherein the locking ring is adapted to be received in a generally cylindrical cavity within the prosthetic head.

9. The prosthesis of claim 8, wherein the generally cylindrical cavity is concentric with the head socket.

10. The prosthesis of claim 7, wherein the locking ring comprises an outer wall which corresponds to an inner wall of the generally cylindrical cavity, and wherein the outer wall of the locking ring comprises a locking surface for engaging a corresponding locking surface on the inner wall of the generally cylindrical cavity for locking the ring within the cavity of the head,
    wherein the locking ring retains the patrix member within the socket between the locking ring and the head socket with a force sufficient to lock the patrix member securely and rigidly in place relative to the stem and the head, wherein the force is distributed around at least one ring of contact between the patrix member and the locking ring and at least one ring of contact between the patrix member and the head socket.

11. The prosthesis of claim 10, wherein the locking surface comprises threads.

12. The prosthesis of claim 7, wherein the patrix member is welded to the second end of the stem, and wherein the locking ring is placed on the second end of the stem prior to welding the patrix member to the stem.

13. The prosthesis of claim 7, wherein the second end of the stem comprises a threaded male end and wherein the patrix member comprises an axial threaded bore for engaging the corresponding threads on the male end of the stem for securely attaching the patrix member to the stem, wherein the locking ring is placed on the second end of the stem prior to attaching the patrix member to the stem.

14. The prosthesis of claim 7, wherein the head socket is frusto-conical and wherein the diameter of the frusto-conical socket decreases toward the interior of the head.

15. The prosthesis of claim 14, wherein the axial bore of the locking ring comprises a tapered bore, wherein the diameter of the tapered bore increases toward the patrix member.

16. The prosthesis of claim 1, wherein the patrix member comprises a generally spherical ball.

17. The prosthesis of claim 1, wherein the prosthesis is adapted to replace the glenohumeral joint, wherein the elongate stem is adapted to be received in the humeral canal of a patient's humerus and wherein the prosthesis head is adapted to correspond to the general size and shape of a patient's humeral head and to articulate to the glenoid cavity of a patient's scapula.

18. A modular humeral prosthesis for replacement of the humeral head of a A humerus, comprising:
    (a) an elongate stem adapted to be implanted within the humeral canal of a resected humerus and having a generally spherical ball on a proximal end of the stem;
    (b) a head adapted to approximate the size and shape of a humeral head and adapted to cooperate with the glenoid cavity of a patient's shoulder, wherein the head comprises
        a generally cylindrical cavity recessed within an underside of the head, wherein the generally cylindrical cavity comprises an internal wall having threads on the surface of the internal wall, and
        a frusto-conical socket located in the head and concentric with the generally cylindrical cavity, wherein the socket provides a housing for receiving the generally spherical ball and is positioned so that an axis of revolution of the head is offset with respect to the center of the ball;
    (c) a locking ring adapted to lock the head to the stem in a desired orientation and fitted around the proximal end of the stem distal to the ball and having external threads adapted to cooperate with the internal threads of the generally cylindrical cavity, wherein the locking ring further comprises a tapered bore for receiving the proximal end of the stem and accommodating a portion of the ball, and
        wherein the locking ring retains the ball within the socket between the locking ring and the head socket with a force sufficient to lock the ball securely and rigidly in place relative to the stem and the head, wherein the force is distributed around at least one ring of contact between the ball and the locking ring and at least one ring of contact between the ball and the head socket.

19. A system for surgical replacement of a joint articulating surface of a bone comprising:
    (a) a selection of implant stems of various lengths and diameters, each having a first end adapted to be received within the medullary canal of a resected bone and a second end adapted for attachment to a generally spherical ball and locking ring;
    (b) at least one patrix member having a generally spherical surface and adapted for attachment to the second end of an implant stem selected from (a);
    (c) a selection of implant heads of various heights and diameters adapted to approximate the size and shape of the joint articulating surface requiring replacement, each having a first surface adapted to cooperate with a corresponding joint surface and a second surface comprising a recessed socket for receiving the patrix member, wherein said socket is concentric to a generally cylindrical cavity;
    (d) at least one locking ring adapted to lock an implant stem selected from (a) to an implant head selected from (c) in a desired orientation to form an implant prosthesis, wherein the locking ring is adapted to fit over the second end of the implant stem and accommodate a portion of the patrix member and adapted to be received within the generally cylindrical cavity of the implant head
        wherein the locking ring retains the patrix member within the head socket between the locking ring and the head socket with a force sufficient to lock the patrix member securely and rigidly in place relative to the stem and the head, wherein the force is distributed around at least one ring of contact between the patrix member and the locking ring and at least one ring of contact between the patrix member and the head socket;
    (e) a selection of trial stems of various lengths and diameters corresponding to the lengths and diameters of the implant stems, each having a first end adapted to be received in the medullary canal of the resected bone and second end attached to a patrix member having a generally spherical surface and a locking ring, wherein the patrix member of the trial stem comprises an axial bore for engaging a device for extracting an assembled trial prosthesis from a patient's bone, and wherein the locking ring of the trial stem comprises an external driving surface for engaging a driver;
    (f) a selection of trial heads of various heights and diameters corresponding to the heights and diameters of the implant heads, each having a first surface adapted to cooperate with a corresponding joint surface and a second surface comprising a recessed socket for receiving the patrix member of the trial stem and a concentric generally cylindrical cavity for receiving the locking ring, wherein the trial head further comprises an axial bore extending through the head, socket and generally cylindrical cavity for accommodating a device for extracting the assembled trial prosthesis from a patient's bone;
    (g) a transfer device for assembling the head and stem of the implant prosthesis in the same orientation as the head and stem of the trial prosthesis after extraction of the trial prosthesis from the patient's bone.

20. The system of claim 19, wherein the patrix member of the implant prosthesis and trial prosthesis comprises a generally spherical ball.

21. The prosthesis of claim 19, wherein the second end of each implant stem comprises a threaded male end and wherein the patrix member comprises an axial threaded bore for engaging the corresponding threads on the male end of the stem for securely attaching the patrix member to the stem, wherein the locking ring is placed on the second end of the stem prior to attaching the patrix member to the stem.

22. The system of claim 19, wherein each implant stem comprises a patrix member and a locking ring, wherein the patrix member is welded to the second end of the stem, and wherein the locking ring is placed on the second end of the stem prior to welding the patrix member to the stem.

23. The system of claim 19, wherein the trial heads are plastic.

24. The system of claim 23, wherein the plastic is color coded to correspond to the various heights and diameters of the trial heads.

25. The system of claim 19, wherein the transfer device allows the extracted trial prosthesis and an implant prosthesis to be mounted in the device simultaneously.

26. The system of claim 19, wherein the transfer device comprises a base unit adapted to receive a head retaining component;

a head retaining component having a two adjacent concave recessions, wherein a first concave recession receives the head of the trial prosthesis and a second concave recession receives the head of the implant prosthesis, and wherein the device allows matching the orientation of the implant head to the orientation of the trial head;

a plate, wherein the plate is placed over the heads to hold the heads in position;

a stem unit, comprising a four bar linkage connecting two cylinders, wherein each cylinder is hollow and adapted to receive a cylinder insert having an axial bore for receiving and retaining the stems of the trial and implant prostheses, and wherein the stem unit allows the implant stem to be manipulated to attain the same orientation of the trial stem.

27. The system of claim 26, wherein the head retaining component is adapted to receive trial and implant heads of a specific height and diameter.

28. The system of claim 27, wherein the head retaining component is plastic.

29. The system of claim 28, wherein the plastic is color coded to correspond to the various heights and diameters of the trial and implant heads.

30. The system of claim 26, wherein the cylinder inserts are adapted to receive trial and implant stems of a particular diameter.

31. The system of claim 30, wherein the cylinder inserts are plastic.

32. The system of claim 31, wherein the plastic is color coded to correspond to the various diameters of the trial and implant stems.

33. A method for replacing a joint articulating portion of a bone in a patient comprising:

(a) resecting an end of the patient's bone;

(b) selecting a trial stem having a length and diameter that corresponds to the length of the resected bone and the diameter of the medullary canal of the resected bone, wherein the trial stem comprises first end adapted to be received in the medullary canal and second end attached to a locking ring and a patrix member having a generally spherical surface;

(c) selecting a trial head having a height and diameter that corresponds to the height and diameter of the joint articulating surface of the bone being replaced; wherein the head comprises a recessed socket for receiving the patrix member of the trial stem, and a generally cylindrical cavity concentric to the socket for receiving and engaging the locking ring;

(d) loosely assembling the trial prosthesis by placing the patrix member within the socket and engaging the locking ring within the generally cylindrical cavity of the trial head;

(e) implanting the assembled trial prosthesis into the patient's bone and testing various orientations of the trial head and stem;

(f) repeating steps (c) through (e) as necessary to select a desired head size and a desired orientation;

(g) locking the selected trial head and stem in the desired orientation;

(h) extracting the locked trial prosthesis from the patient;

(i) mounting the trial prosthesis in a transfer device;

(j) selecting an implant head and stem that correspond to the size and shape of the trial head and stem, wherein the implant head comprises a first surface adapted to cooperate with a joint surface and a second surface comprising a generally cylindrical cavity and a recessed socket, and wherein the implant stem comprises a first end adapted to be received within the medullary canal of the resected bone and a second end attached to a patrix member having a generally spherical surface and adapted to be received in the recessed socket of the head;

(k) loosely assembling the implant head and stem to form an implant prosthesis and mounting the implant prosthesis in the transfer device;

(l) using the transfer device to manipulate the stem of the implant prosthesis to match the orientation of the locked trial prosthesis;

(m) locking the implant prosthesis head and stem in the selected orientation using a driver to engage a locking ring fitted around the neck of the implant stem and adapted to engage the generally cylindrical cavity in the implant head and a portion of the patrix member, and wherein the locking ring retains the patrix member within the head socket between the locking ring and the head socket with a force sufficient to lock the patrix member securely and rigidly in place relative to the stem and the head, wherein the force is distributed around at least one ring of contact between the patrix member and the locking ring and at least one ring of contact between the patrix member and the head socket; and (n) removing the locked implant prosthesis from the transfer device and implanting the prosthesis into the patient's resected bone.

* * * * *